US006613097B1

United States Patent
Cooper

(10) Patent No.: US 6,613,097 B1
(45) Date of Patent: Sep. 2, 2003

(54) SWING PHASE CONTROL FOR AN ARTIFICIAL LOWER LIMB

(75) Inventor: John Edwin Cooper, Haslemere (GB)

(73) Assignee: Ohio Willow Wood Company, Mount Sterling, OH (US)

( * ) Notice: Subject to any disclaimer, the term of this patent is extended or adjusted under 35 U.S.C. 154(b) by 0 days.

(21) Appl. No.: 09/579,437

(22) Filed: May 26, 2000

(30) Foreign Application Priority Data

Jun. 28, 1999 (GB) ............................................. 9914989

(51) Int. Cl.[7] ............................. A61F 2/64; A61F 2/62
(52) U.S. Cl. ........................................... 623/44; 623/39
(58) Field of Search ............................. 623/44, 45, 43, 623/46, 39, 26; 188/285, 322.19, 282.3, 282.2, 314

(56) References Cited

U.S. PATENT DOCUMENTS

| 5,376,137 A | * | 12/1994 | Shorter et al. | ................. | 623/44 |
| 5,443,521 A | * | 8/1995 | Knoth et al. | ................... | 623/44 |
| 5,746,774 A | * | 5/1998 | Kramer et al. | ................. | 623/39 |
| 5,948,021 A | * | 9/1999 | Radcliffe | ..................... | 623/44 |
| 6,113,642 A | * | 9/2000 | Petrofsky et al. | ............. | 623/24 |

FOREIGN PATENT DOCUMENTS

| DE | 10 75 277 | 2/1960 |
| EP | 0 549 855 | 7/1993 |
| EP | 0 668 065 | 8/1995 |
| EP | 1 262 155 | 12/2002 |
| GB | 2 253 791 | 9/1992 |
| GB | 2 338 653 | 12/1999 |
| WO | WO 00 27318 | 5/2000 |

* cited by examiner

*Primary Examiner*—Corrine McDermott
*Assistant Examiner*—Alvin Stewart
(74) *Attorney, Agent, or Firm*—Oblon, Spivak, McClelland, Maier & Neustadt, P.C.

(57) ABSTRACT

A hydraulic swing phase control unit for an artificial lower limb including a thigh part and a shin part connected at a knee joint, includes a hydraulic cylinder connected to one of the thigh part and the shin part, a piston movable in the hydraulic cylinder and connected to the other of the thigh part and the shin part, a fluid passage positioned to pass hydraulic fluid pressurized by movement of the piston in the hydraulic cylinder; and a variable sharp edged orifice at the fluid passage. The variable orifice is formed from a sharp edged orifice and a manually rotatable sleeve positioned to at least partly overlap the orifice. At least one low restriction fluid passage in the cylinder is fluidically connected in parallel with the variable sharp edged orifice to permit minimal resistance to movement of the piston during a portion of the movement thereof.

19 Claims, 6 Drawing Sheets

SWING PHASE CONTROL FOR AN ARTIFICIAL LOWER LIMB

BACKGROUND OF THE INVENTION

1. Field of the Invention

This invention relates to a swing phase control for an artificial lower limb and to a prosthesis including the control.

2. Discussion of the Background

The use of hydraulic swing phase controls in artificial above knee limbs is well known. They commonly comprise a piston and cylinder assembly connected to the thigh and the shin part of the limb with the line of action of the control being offset from the center of rotation of the knee and with the two ends of the cylinder connected by variable orifices and check valves so that adjustment of the orifices changes the damping provided by the control and thereby modifies the swing phase behavior of the limb. However existing controls commonly have continuous fluid communication through narrow passages between the two ends of the cylinder, which results in there being too much resistance during those parts of the swing phase when no resistance is necessary. Furthermore, existing designs use orifices that operate with laminar flow so that their hydraulic resistance is inherently sensitive to changes in fluid temperature; thus changes in the swing phase characteristics of the limb occur when the fluid temperature changes. Moreover, such orifices have a linear relationship between pressure drop and flow so that their resistance rises linearly with the angular velocity of the shin whereas the amount of energy that has to be dissipated rises with the square of the angular velocity of the shin.

SUMMARY OF THE INVENTION

It is an object of this invention to provide a simplified swing phase control that also improves on the above characteristics.

According to the present invention there is provided a hydraulic swing phase control unit which in one embodiment provides minimal resistance to shin flexion until, at a predetermined angle of flexion which corresponds to the toe off position, it provides adjustable resistance to flexion, and in the reverse direction provides minimal resistance to extension until at another predetermined angle which is near to the fully extended position, it provides adjustable resistance to extension.

In a second embodiment of the invention there is provided a hydraulic swing phase control unit which provides minimal resistance to shin flexion until, at a predetermined angle of flexion which corresponds to the toe off position, it provides adjustable resistance to flexion, but at a further predetermined angle corresponding to the maximum angle of flexion that occurs during normal walking, it ceases providing resistance to flexion. It thereafter resists extension in the same manner described for the first embodiment. There is thus minimal resistance to either flexion or extension when the knee is in the position normally adopted for sitting or kneeling.

In both embodiments an adjustable sharp edged orifice is provided to adjust the resistance to flexion or to extension. It is well known that the characteristics of sharp edged orifices are relatively insensitive to changes in temperature. Furthermore their pressure drop increases in proportion to the square of the flow so that the resistance provided by the control rises with walking speed at the same rate as the amount of energy that has to be dissipated.

In both embodiments the internal reservoir pressure is maintained by a spring loaded rolling diaphragm although similar means such as a spring loaded piston or a bellows could perform the same function. Also, in both embodiments a spring return feature can be added to the control units.

It should be noted that the controls are suitable for use with either monocentric or polycentric knees. It should be further noted that the control units hereafter described are illustrated with their rod end uppermost and connected to the thigh whereas their effectiveness is unimpaired if the arrangement is inverted and the rod end is connected to the shin.

The control units may be connected with their effective line of action posterior to the knee axis in which case the unit retracts when the shin is flexed; or they may connected with their effective line of action anterior to the knee axis in which case the unit extends when the shin is flexed. It will be noted that these two ways of connecting the units result in different piston displacement and offset characteristics as the shin is flexed.

The control units may be arranged with either of the described embodiments combined with their line of action being either anterior or posterior to the knee axis. However for simplicity, but to still illustrate the principles involved, two combinations arising from the two embodiments and two thigh connection positions are hereafter described by way of reference to the following drawings.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
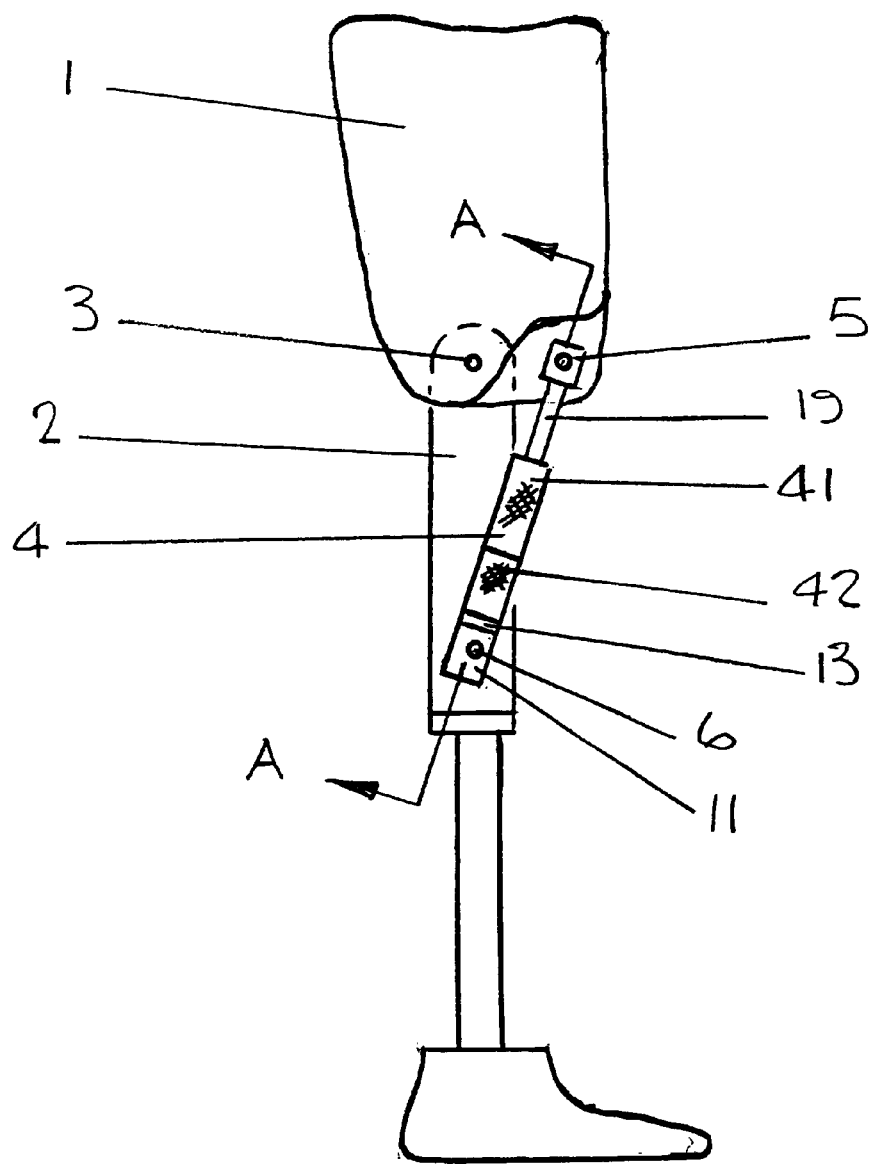
FIG. 1 is a diagrammatic view of a unit installed with its line of action passing anterior to the knee axis.

Referring to FIG. 1, thigh piece 1 is connected by knee axis 3 to shin assembly 2, which assembly comprises both a shin and a foot. Control unit 4 is pivotally connected to said thigh piece 1 by boss and pin 5, and to said shin assembly by pins 6. It can be seen that the effective line of action of control unit 4 passes anterior to knee axis 3 and that the unit extends when the said shin assembly is flexed.

Figure 2:
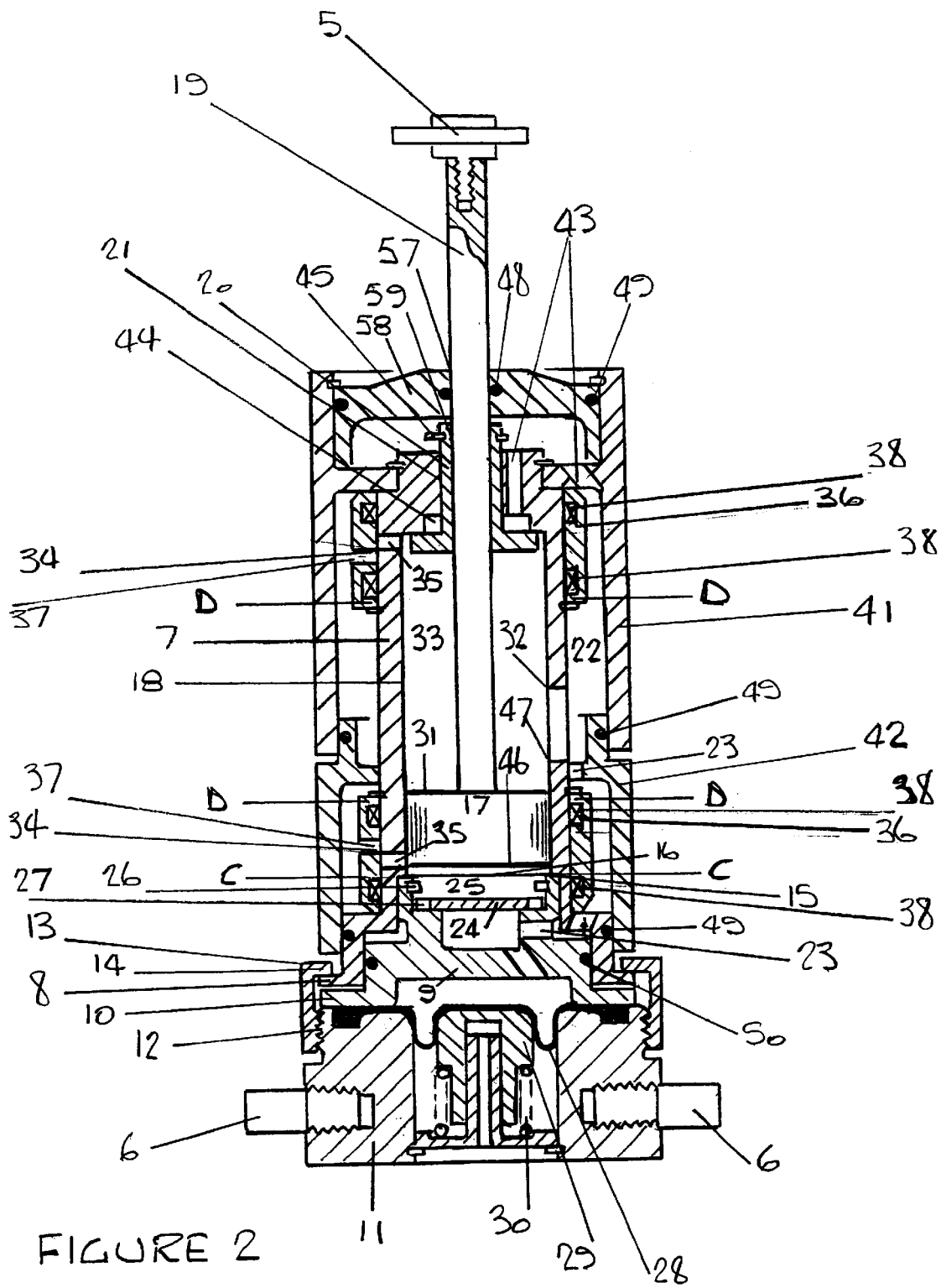
FIG. 2 is a cross section of a unit taken along line A—A of FIG. 1 and is intended to illustrate the principles of the first embodiment.

Referring to FIG. 2, the control unit comprises a cylinder 7 which has flange 8, valve housing 9 which has flange 10, trunnion housing 11 which has thread 12. The cylinder 7, valve housing 9 and trunnion housing 11 are united by a ring 13 which has flange 14 bearing on flange 8 and an internally threaded portion which engages with thread 12 of trunnion housing 11. A rolling diaphragm 28 is thereby clamped between the flange 10 and the trunnion housing 11. The rolling diaphragm 28 is energized by a piston 29 and spring 30. Cylinder 7 has at its lower end an enlarged bore and shoulder 15 which abuts face 16 of valve housing 9 so that when ring 13 is tightened on thread 12 of trunnion housing 11, flange 14 of ring 13 tightens on flange 8 of cylinder 7 so that cylinder 7, valve housing 9 and trunnion housing 11 become a secure semi-permanent assembly and there remains a small gap between flange 8 of cylinder 7 and flange 10 of valve housing 9.

Hydraulic fluid is contained within the unit by elastomer seals 48, 49, 50 and rolling diaphragm 28. It will be noted that the seals are only exposed to reservoir pressure and that no elastomer seals are used to contain the higher pressures that are generated within the cylinders when the unit is providing damping resistance.

Piston 17 slides in bore 18 of cylinder 7 and is fixed to rod 19 which slidably extends through bore 57 of seal housing 58. Passages 43 communicate the bore 18 and a surrounding annular hydraulic fluid reservoir 22 with a space defined by the seal housing 58. Rod 19 also slidably extends through bore 59 of valve 20, with said valve 20 itself slideably engaged within reduced diameter bore 21 of cylinder 7. The valve 20 can move to selectively open or close the annular space 44 communicating between bore 18 and the space defined by the seal housing 58. Boss and pin 5 are threadably connected to rod 19 and pin 6 is threadably connected to trunnion housing 11.

The hydraulic fluid reservoir 22 also communicates via passages 23 and disc valve 24 with cylinder space 25, and with bore 18 through a low restriction port with edges 32 and 47, and via variable orifices 34. Hydraulic fluid in the device can therefore flow into and out of the bore 18. There are variable orifices at both the top and the bottom of the bore 18. Each variable orifice 34 comprises sharp edged passage hole 35, sleeve 36, sharp edged slot 37, and piston rings 38 intended to prevent excessive longitudinal leakage between the bore of sleeve 36 and the outside diameter of cylinder 7.

Thus, it can be seen that the upper variable orifice 34, the passages 43 and the port having the edges 32 and 37, form fluidically parallel connections between the upper chamber 33 of the cylinder 7 and the annular reservoir 22. Movement of the piston causes selective closure of these parallel connections, and so varies the resistance of the piston to movement within the cylinder, and knee flexure or extension. Conversely, lower variable orifice 34, and the series connection of the passage 23 and the valve 24, form fluidically parallel connections between the lower chamber 25 of the cylinder 7 and the annular reservoir 22. Movement of the piston causes selective closure of these parallel connections, and so varies the resistance of the piston to movement within the cylinder, and knee flexure or extension.

Figure 6:
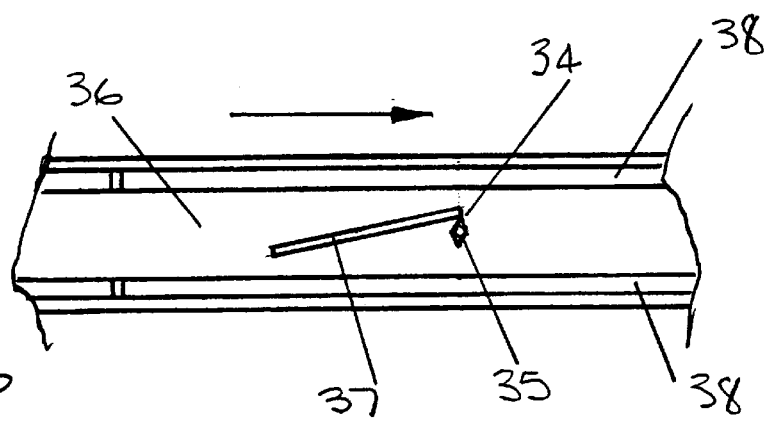
FIG. 6 is a developed view of the variable orifice.

Referring to FIG. 6, there is shown a developed view of the contiguous surfaces of sleeve 36 and cylinder 7. It can be seen that as sleeve 36 is rotated in the direction of the arrow, the size of variable orifice 34 increases because the size of said orifice is determined by the overlapping area of passage hole 35 and slot 37. It will be noted that variable orifice 34 is sharp edged so that its pressure/flow characteristic is relatively insensitive to temperature change and, moreover, said characteristic provides a change in pressure drop that varies in proportion to the square of the flow. Therefore, the resistance of the unit is proportional to the angular velocity of the leg. When slot 37 has moved half of the potential travel illustrated; the maximum orifice size is reached and so this half travel represents the adjustment range between maximum and minimum resistance. However further movement of slot 37 over the second half of the illustrated travel reduces the orifice size to zero; thus the same direction of adjustment can be provided whichever way that sleeve 36 is assembled on cylinder 7. Hole 35 and slot 37 may be arranged so that the whole of the travel is required to adjust from minimum to maximum, in which case adjustment sensitivity is improved but the reversible assembly facility is lost. Hole 35 is shown as "V" shaped, however it could also be other shapes depending upon the adjustment sensitivity required. Similarly slot 37 is shown with a straight and parallel cut, however it could also be produced with a "V" shaped cross section which would modify the adjustment sensitivity.

It can be seen that adjustment of the variable orifice 34 is achieved by rotating sleeve 36 on the outside diameter of cylinder 7.

Figure 7:
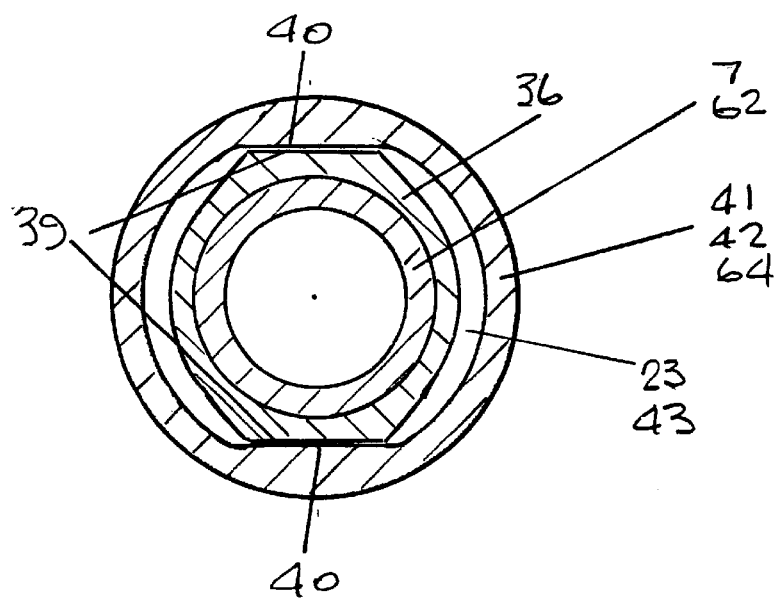
FIG. 7 is a part sectional view taken along lines D—D of FIG. 2 and FIG. 4.

Referring to FIG. 7, flats 39 are formed on a flanged projection of sleeve 36 and fit inside flats 40 inside both cylinder 41 and cylinder 42. Thus when cylinder 41 and/or cylinder 42 are externally rotated, then the corresponding sleeve 36 is also rotated and there then occurs a change in the damping force provided by the unit, and the swing phase characteristics of the limb are thereby changed.

Figure 5:
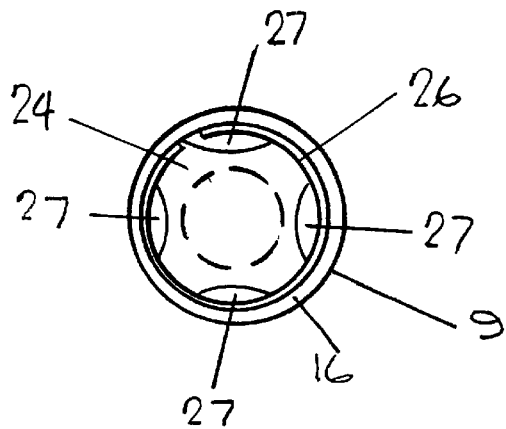
FIG. 5 is a part view taken along line C—C of FIG. 2 and FIG. 4.

The valve 24 is shown in detail in FIG. 5. It has the form of a disc with cut-outs 27, and is retained by a spring ring 26. It permits one way flow into the cylinder space 25.

Referring to FIG. 2, when shin and foot assembly 2 commences flexion, piston 17 moves upwards and draws fluid from reservoir 22 via passages 23 and valve 24 into cylinder space 25. The flow causes valve 24 to rise and contact spring ring 26. Referring to FIG. 5, fluid enters cylinder space 25 via cut-outs 27 of valve 24. The internal volume change caused by rod 19 rising is compensated for by rolling diaphragm 28 which is energized by piston 29 and spring 30. The load from said spring 30 maintains the reservoir pressure at slightly above atmospheric.

As piston 17 rises it meets minimal resistance until piston end 31 reaches port edge 32, which occurs at the piston displacement that corresponds to the position of the shin and foot assembly 2 at the instant of toe off. As the shin and foot assembly 2 continue to flex, piston 17 continues to rise and forces fluid through valve 20, thus causing it to close. Once valve 20 closes, the fluid in cylinder space 33 becomes pressurized and thus creates a force which resists further flexion. The fluid now being displaced by piston 17 is forced through the sharp edged variable orifice 34. It will be noted that piston 17 is shown as a plain cylinder having a close fit in bore 18, however a slightly smaller cylinder with a piston ring could perform the same function.

At the end of shin flexion and upon the start of shin extension, piston 17 moves downwards and fluid is drawn from reservoir 22 via passages 43 into annular chamber 44. Valve 20 opens by an amount determined by spring ring 45 and fluid enters cylinder space 33. The internal volume changes caused by rod 19 retracting are compensated for by rolling diaphragm 28 in the manner previously described but in the reverse direction. As piston 17 moves downwards it provides minimal resistance until piston edge 46 reaches port edge 47, which event occurs at a piston displacement that corresponds to the position of the shin assembly near the fully extended position. As piston 17 continues to descend, valve 24 closes and fluid is forced through variable orifice 34, causing the fluid in cylinder space 25 to become pressurized and thus creating a damping force which resists further extension of the limb. The adjustment of said damping force is then the same as previously described for the flexion stroke.

Figure 9:
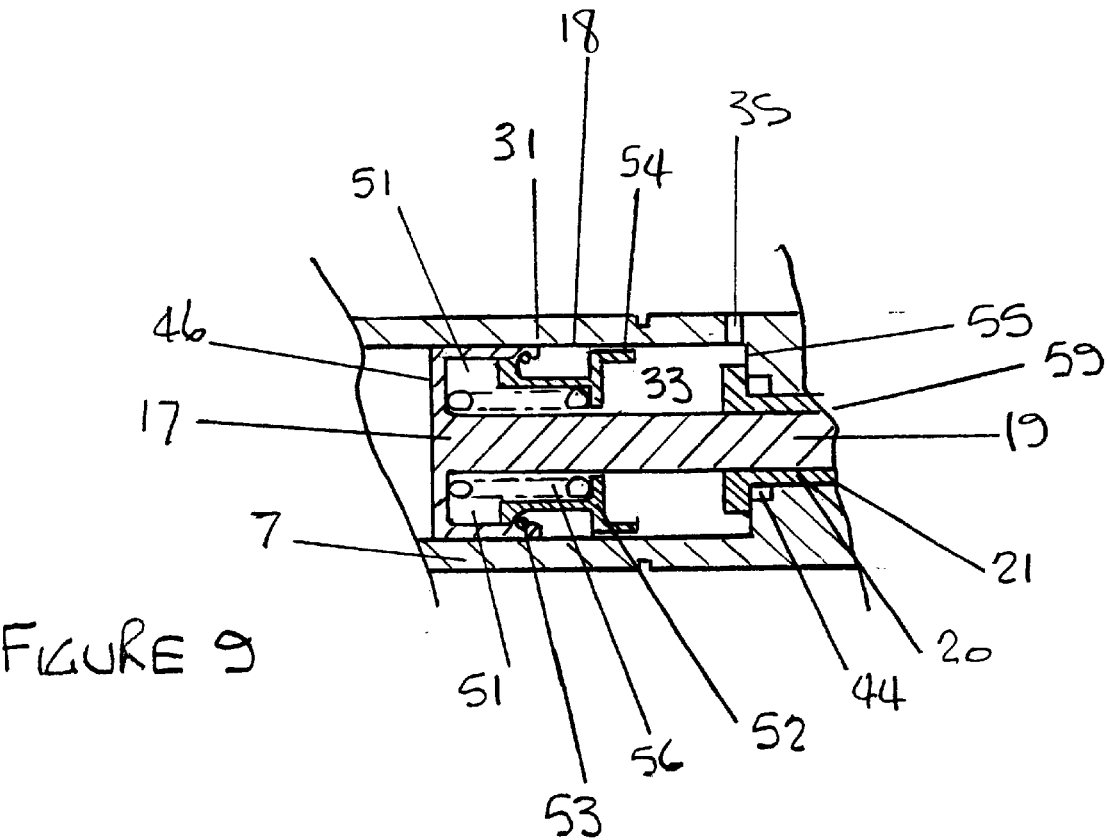
FIG. 9 is a part sectional view taken along line A—A of FIG. 1.

It is sometimes desirable to provide a spring returning force at the end of limb flexion. Such a force can be provided as shown on FIG. 9. Piston 17 then has an annular space 51 into which fits buffer 52 which is retained in said annular space by spring ring 53. Buffer 52 has an annular projection 54 which is larger than the flange of valve 20 so that said valve 20 can still open when annular projection 54 is in contact with end wall 55. Spring 56 is preloaded to the required level and when annular projection 54 contacts end wall 55, the spring 56 is further compressed as piston 17 moves upwards and a returning force is thus generated.

Figure 3:
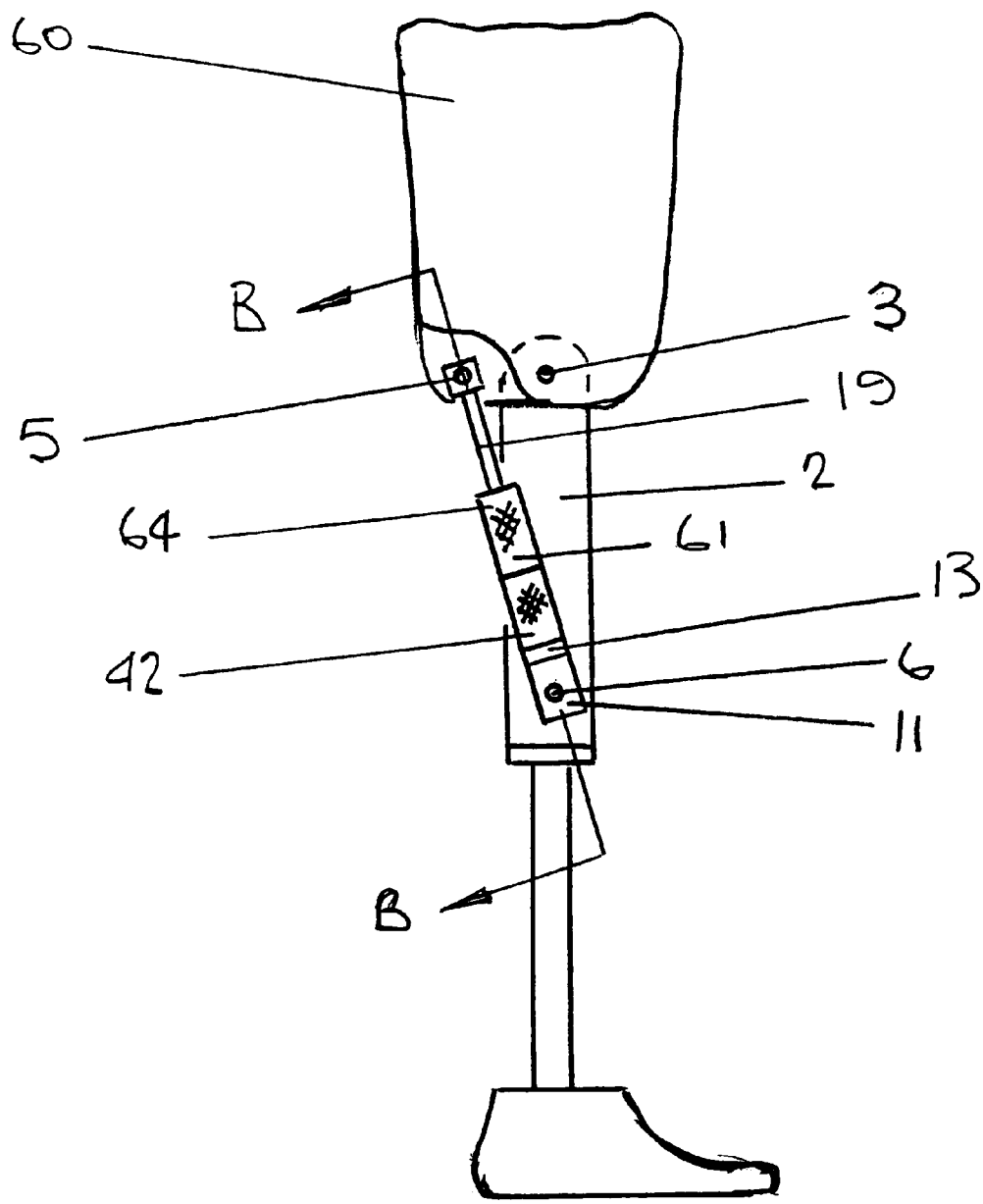
FIG. 3 is a diagrammatic view of a unit installed with its line of action passing posterior to the knee axis.

Referring now to FIG. 3, thigh piece 60 is connected to shin assembly 2 by knee axis 3. Control unit 61 is pivotally connected to thigh piece 60 and to shin assembly 2 in the same manner as previously described, however it can be seen that the effective line of action of control unit 61 here passes posterior to the knee axis 3 and that the unit retracts when said shin assembly is flexed.

Figure 4:
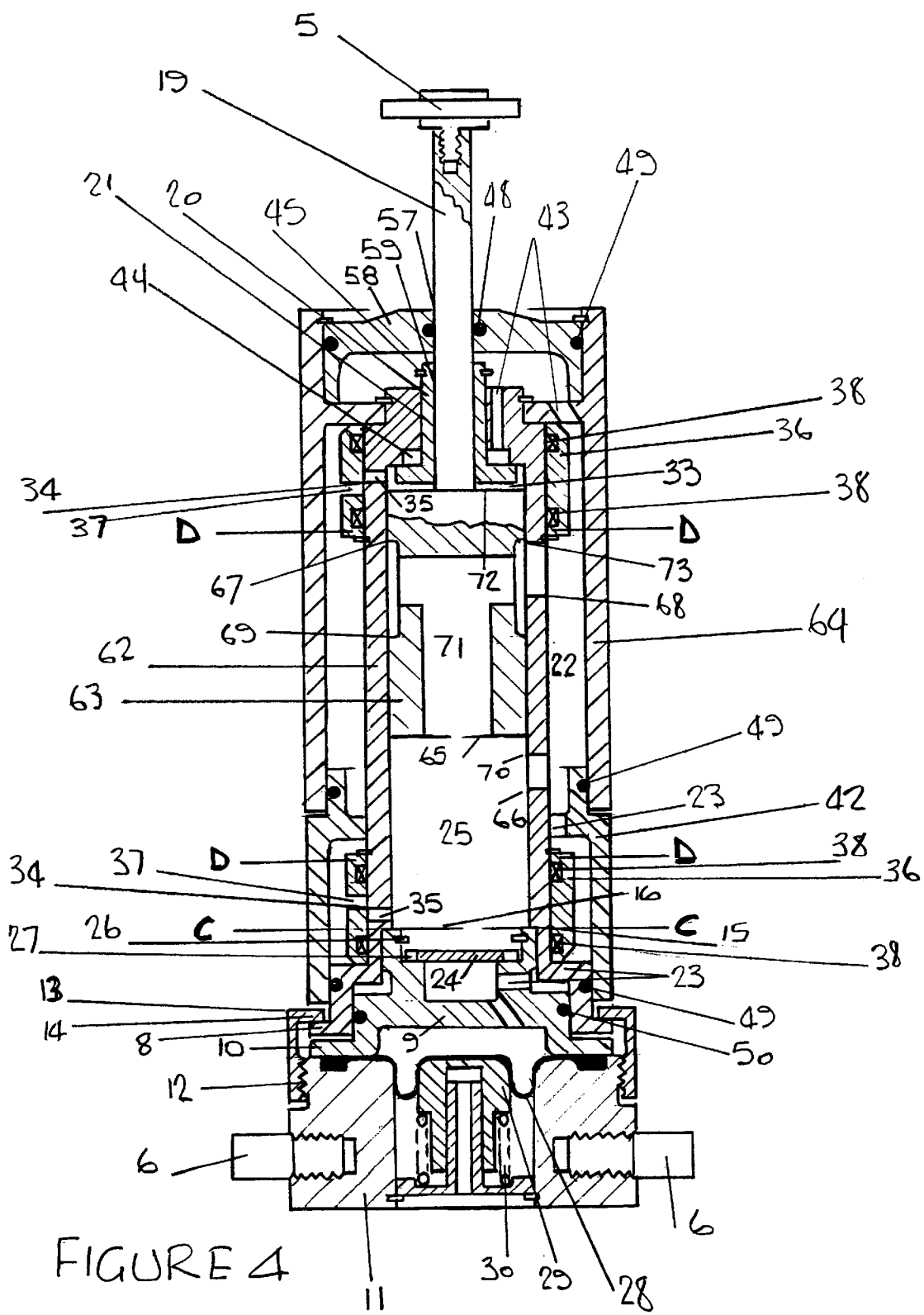
FIG. 4 is a cross section of a unit taken along line B—B of FIG. 3 and is intended to illustrate the principles of the second embodiment.

Referring to FIG. 4, the internal structure is the same as previously described save that cylinder 62 replaces cylinder 7, piston 63 replaces piston 17 and cylinder 64 replaces cylinder 41. Piston 63 has an annular groove with edges 67 and 69. An internal passage 71 of the piston communicates this annular groove with the bottom surface 65 of the piston. Note that these alternative parts are necessary to accommodate the different displacements and port arrangements and that all other components are identical to those previously described.

When shin assembly 2 of the second embodiment commences flexion, piston 63 moves downwards and draws fluid from annular reservoir 22 into cylinder space 33 via passages 43 and valve 20 in the same manner as previously described. As piston 63 descends it meets minimal resistance until piston edge 65 reaches port edge 66, and simultaneously piston edge 67 reaches port edge 68, which occurs at the piston displacement that corresponds to the position of shin assembly 2 at the instant of toe off. As shin assembly 2 continues to flex, piston 63 descends further, causing fluid in cylinder space 25 to become pressurized, thus creating a force which resists flexion. The level of resistance can be adjusted by variable orifice 34 in the same manner as previously described.

When shin assembly 2 is flexed to a further position which occurs at the piston displacement that corresponds to the maximum angle of flexion that occurs in normal walking, then piston edge 69 reaches port edge 70 and the fluid in cylinder space 25 becomes free to flow through passages 7 into reservoir 22, and there is thus no further resistance to flexion.

At the end of flexion and upon the start of extension, piston 63 moves upwards with fluid being drawn into cylinder chamber 25 in the manner previously described, and with the unit providing minimal resistance until piston edge 72 reaches port edge 73, which occurs at a piston displacement near to the fully extended position, and the unit starts to resist extension in the manner previously described.

Figure 8:
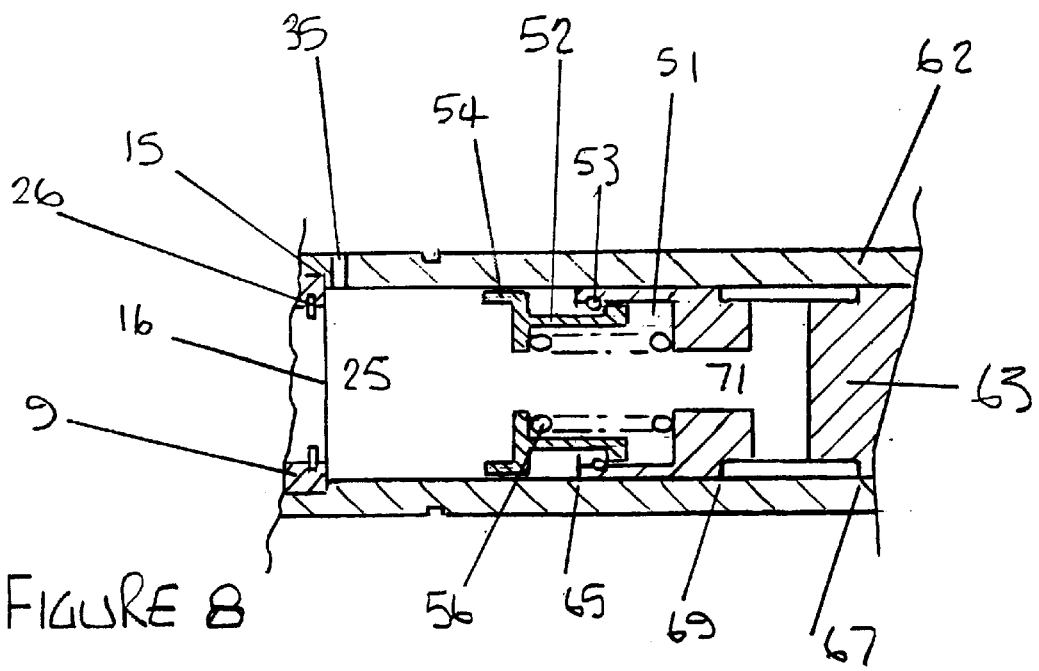
FIG. 8 is a part sectional view taken along line B—B of FIG. 3.

When a spring return force is desired for this second embodiment it can be provided in the manner illustrated on FIG. 8 where the action is the same as previously described save that annular projection 54 contacts the abutment surface provided by face 16 of valve housing 9.

Obviously, numerous modifications and variations of the present invention are possible in light of the above teachings. It is therefore to be understood that within the scope of the appended claims, the invention may be practiced otherwise than as specifically described herein.

What is claimed:

1. A hydraulic swing phase control unit for an artificial lower limb, comprising:

means for providing minimal resistance to shin flexion until a predetermined angle of flexion which corresponds to the toe off position is reached;

means for providing adjustable resistance to flexion after the toe off position is reached;

means for providing minimal resistance to shin extension until predetermined angle which is near to the fully extended position is reached; and means for providing adjustable resistance to extension after the predetermined angle is reached during shin extension.

2. The hydraulic swing phase control unit of claim 1, further comprising means for providing a spring returning force at the end of shin flexion.

3. A hydraulic swing phase control unit for an artificial lower limb, comprising:

means for providing minimal resistance to shin flexion until a predetermined angle of flexion which corresponds to the toe off position is reached;

means for providing adjustable resistance to flexion after the toe off position is reached; and means for subsequently providing minimal resistance to shin flexion when a predetermined angle which corresponds to sitting or kneeling is reached.

4. The hydraulic swing phase control unit of claim 3, further comprising:

means for providing minimal resistance to shin extension until predetermined angle which is near to the fully extended position is reached; and means for providing adjustable resistance to extension after the predetermined angle is reached during shin extension.

5. The hydraulic swing phase control unit of claim 3, further comprising means for providing a spring returning force at the end of shin flexion.

6. A hydraulic swing phase control unit for an artificial lower limb including a thigh part and a shin part connected at a knee joint, comprising:

a hydraulic cylinder connected to one of the thigh part and the shin part;

a piston movable in said hydraulic cylinder and connected to the other of the thigh part and the shin part;

a fluid passage positioned to pass hydraulic fluid pressurized by movement of said piston in said hydraulic cylinder; and a variable sharp edged orifice at said fluid passage, said variable sharp edged orifice providing a change in a pressure from therethrough which varies in proportion to a square of a rate of flow of fluid therethrough.

7. The hydraulic swing phase control unit of claim 6, wherein said variable orifice comprises:

a sharp edged orifice at said fluid passage; and a manually rotatable sleeve positioned to at least partly overlap said orifice.

8. The hydraulic swing phase control unit of claim 6, further comprising at least one low restriction fluid passage in said cylinder, said low restriction fluid passage being fluidically connected in parallel with said variable sharp edged orifice, to permit minimal resistance to movement of said piston during a portion of the movement thereof.

9. The hydraulic swing phase control unit of claim 8, further comprising a fluid passage in said piston and in fluid communication with said low restriction fluid passage during a portion of the movement of said piston.

10. The hydraulic swing phase control unit of claim 6, wherein the unit is connected to the thigh part and the shin part such that an effective line of action of the unit is anterior to the knee axis.

11. The hydraulic swing phase control unit of claim 6, wherein the unit is connected to the thigh part and the shin part such that an effective line of action of the unit is posterior to the knee axis.

12. The hydraulic swing phase control unit of claim 6, wherein there are two of said fluid passages positioned to pass hydraulic fluid pressurized by movement of said piston in said hydraulic cylinder, and one of said variable sharp edged orifices at each said fluid passage, wherein said two fluid passages are positioned to be on mutually opposite sides of said piston.

13. The hydraulic swing phase control unit of claim 6, wherein said unit's performance is minimally sensitive to temperature changes.

14. The hydraulic swing phase control unit of claim 6, wherein said unit's resistance is proportional to the angular velocity of the leg.

15. A hydraulic swing phase control unit for an artificial lower limb, comprising:

means for providing minimal resistance to shin flexion until a predetermined angle of flexion which corresponds to the toe off position is reached;

means for providing increased resistance to flexion after the toe off position is reached; and means for subsequently providing minimal resistance to shin flexion.

16. The hydraulic swing phase control unit of claim 15, wherein said means for providing increased resistance to flexion after the toe off position is reached, comprises means for providing variable resistance to flexion after the toe off position is reached.

17. A hydraulic swing phase control unit for an artificial lower limb, comprising:

means for providing minimal resistance to shin flexion until a predetermined angle of flexion which corresponds to the toe off position is reached;

means for providing increased resistance to flexion after the toe off position is reached;

means for providing minimal resistance to shin extension until a predetermined angle which is near to the fully extended position is reached; and means for providing increased resistance to extension after the predetermined angle is reached during shin extension.

18. The hydraulic swing phase control unit of claim 17, wherein said means for providing increased resistance to flexion after the toe off position is reached, comprises means for providing variable resistance to flexion after the toe off position is reached.

19. The hydraulic swing phase control unit of claim 17, wherein said means for providing increased resistance to extension after the predetermined angle is reached, comprises means for providing variable resistance to extension after the predetermined angle is reached.

* * * * *